United States Patent [19]

Desai et al.

[11] Patent Number: 5,512,576
[45] Date of Patent: Apr. 30, 1996

[54] 2-SUBSTITUTED 1,2,5,-THIADIAZOLIDIN-3-ONE 1,1-DIOXIDES AND COMPOSITIONS AND METHOD OF USE THEREOF

[75] Inventors: Ranjit C. Desai, Towamencin Township, Montgomery County; Dennis J. Hlasta, Lower Salford Township, Montgomery County, both of Pa.

[73] Assignee: Sterling Winthrop Inc., New York, N.Y.

[21] Appl. No.: 348,440

[22] Filed: Dec. 2, 1994

[51] Int. Cl.$^6$ .................. C07D 417/12; A61K 31/41
[52] U.S. Cl. .................. 514/258; 514/233.2; 514/236.2; 514/312; 514/326; 514/362; 544/116; 544/134; 544/279; 544/282; 546/157; 546/209; 546/277; 548/135
[58] Field of Search .................. 548/135; 546/157, 546/277, 209; 544/282, 134, 116, 279; 514/326, 312, 258, 236.2, 233.2, 326

[56] References Cited

U.S. PATENT DOCUMENTS 5,236,917  8/1993  Dunlap et al. .

FOREIGN PATENT DOCUMENTS 547708  6/1993  European Pat. Off. .
4141218  6/1993  Germany .

OTHER PUBLICATIONS

Cha, Biochem. Pharmacol., 1975, 24, 2177–2185.
Groutas et al., Biochemical and Biophysical Research Communications 1994, 198(1), 341–349.
Muller and DuBois, J. Org. Chem. 1989, 54, 4471–4473.
Lee et al., J. Org. Chem. 1989, 54, 3077–3083.
Lee and Kohn, Journal of Pharmaceutical Sciences 1990, 79(8), 716–718.
Hanewacker et al., Arch. Pharm. 1993, 326, 497–498.
Unterhalt and Hanewacker, Arch. Pharm. 1988, 321, 375–376.
Unterhalt and Hanewacker, Arch. Pharm. 1988, 321, 749–751.
Auof et al., Tetrahedron Letters 1991, 32(45), 6545–6546.
Dewynter et al., Tetrahedron 1993, 49(1), 65–76.

Primary Examiner—Robert Gerstl
Attorney, Agent, or Firm—Michael D. Alexander; Paul E. Dupont

[57] ABSTRACT

2-Substituted 1,2,5-thiadiazolidin-3-one 1,1-dioxides, pharmaceutical compositions containing them and methods for the treatment of degenerative diseases utilizing them.

17 Claims, No Drawings

2-SUBSTITUTED 1,2,5,-THIADIAZOLIDIN-3-ONE 1,1-DIOXIDES AND COMPOSITIONS AND METHOD OF USE THEREOF

BACKGROUND OF THE INVENTION (a) Field of The Invention

The invention relates to 2-substituted 1,2,5-thiadiazolidin-3-one 1,1-dioxides, to pharmaceutical compositions containing the same and to the method of use thereof in the treatment of degenerative diseases.

(b) Information Disclosure Statement

The inhibition of proteolytic enzymes by nontoxic reagents is useful in the treatment of degenerative disorders, such as emphysema, rheumatoid arthritis and pancreatitis, in which proteolysis is a substantive element.

Protease inhibitors are widely utilized in biomedical research. Serine proteases are the most widely distributed class of proteolytic enzymes. Some serine proteases are characterized as chymotrypsin-like or elastase-like based upon their substrate specificity.

Chymotrypsin and chymotrypsin-like enzymes normally cleave peptide bonds in proteins at a site at which the amino acid residue on the carboxyl side is typically Trp, Tyr, Phe, Met, Leu or another amino acid residue which contains aromatic or large alkyl side chains.

Elastase and elastase-like enzymes normally cleave peptide bonds at a site at which the amino acid residue on the carboxyl side of the bond is typically Ala, Val, Ser, Leu or other similar, smaller amino acids.

Both chymotrypsin-like and elastase-like enzymes are found in leukocytes, mast cells and pancreatic juice in higher organisms, and are secreted by many types of bacteria, yeast and parasites.

Cha, Biochem. Pharmacol., 1975, 24, 2177–2185, discusses kinetic approaches to the study of the binding of inhibitors to macromolecules, such as enzymes, and methods for the determination of such parameters as the inhibition constants, reaction rates and bound and unbound enzyme concentrations.

Groutas et al., Biochemical and Biophysical Research Communications 1994, 198(1), 341–349 disclose compounds of the formula:

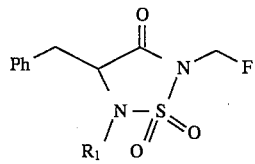

wherein $R_1$ is H, methyl, benzyl, $CH_2COOt$-Bu or $CH_2COOBzl$ and their in vitro inhibitory activity towards human leukocyte elastase.

Muller and DuBois, J. Org. Chem. 1989, 54, 4471–4473 disclose compounds of the formula:

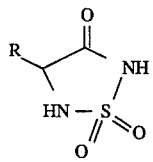

wherein R is H, $CH_3$, benzyl or $(CH_2)_2SCH_3$. The compounds were tested for sweet taste activity and were found to be not sweet or to have sweetness potencies of less than 10 times sucrose.

Lee et al., J. Org. Chem. 1989, 54, 3077–3083 disclose the synthesis of compounds of the formula:

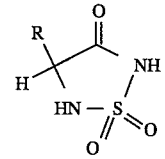

wherein R is phenethyl, phenyl or 1-naphthyl. No utility is disclosed for these compounds.

Lee and Kohn, Journal of Pharmaceutical Sciences 1990, 79(8), 716–718 disclose compounds of the formula:

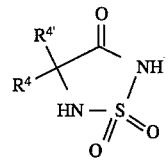

wherein $R^4$ is phenethyl, phenyl or 1-naphthyl and $R^{4'}$ is hydrogen, or $R^4$ and $R^{4'}$ are both phenyl. The compounds were tested for anticonvulsant activity and three of the four compounds were found to be devoid of anticonvulsant activity.

Hanewacker et al., Arch. Pharm. 1993, 326, 497–498 disclose the synthesis of compounds of the formula:

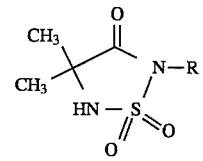

wherein R is $CH_2CH(CH_3)_2$, cyclopropylmethyl, $CH_2Ph$, $(CH_2)_2Ph$, 2-furanylmethyl, 1-naphthylmethyl, or 3-indolylethyl.

Unterhalt and Hanewacker, Arch. Pharm. 1988, 321, 375–376 disclose the synthesis of compounds of the formula:

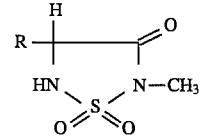

wherein R is hydrogen, methyl, isopropyl, $CH_2CH(CH_3)_2$ or benzyl without an indication of utility.

Unterhalt and Hanewacker, Arch. Pharm. 1988, 321, 749–751 disclose the synthesis of compounds of the formula:

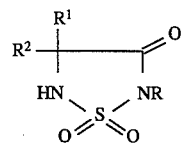

wherein $R=CH_3$, $R^1=H$ and $R^2=$3-indolylmethyl; $R=CH_3$, $R^1=H$, and $R^2=$phenyl; $R=C_2H_5$, $R^1=H$, and $R^2$=phenyl; R=isopropyl, $R^1$=H, and $R^2$=phenyl; R=methyl, $R^1$=$CH_3O(O)CCH_2$, and $R^2$=H; R=$CH_3$, $R^1$=HO(O)$CCH_2$ and $R^2$=H; R=$CH_3$, $R^1$=$C_2H_5$ and $R^2$=phenyl; R=$R^1$= $R^2$=$CH_3$; and R=$C_2H_5$, $R^1$=$R^2$=$CH_3$.

Aouf et al., Tetrahedron Letters 1991, 32(45), 6545–6546 disclose the synthesis of 4-phenylmethyl-1,2,5-thiadiazolidin-3-one 1,1-dioxide.

Dewynter et al., Tetrahedron 1993, 49(1), 65–76 disclose the synthesis of compounds of the formula:

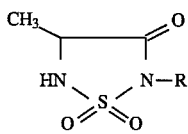

wherein R is $CH_2Ph$ or $CH_2CH(CH_3)$ ($C_2H_5$).

Dunlap et al., U.S. Pat. No. 5,236,917, issued Aug. 17, 1993 disclose a series of 2-substituted saccharin derivatives, such as 4-(1-methylethyl)-2-[(3-oxo-1,2,5-thiadiazolidin-2-yl)methyl] -1,2-benzisothiazol-3(2H)-one S,S,1,1-tetraoxide, 2-(1-methyl-1H-tetrazol-5-yl-thiomethyl)saccharin, and various substituted 2-halomethyl saccharin derivatives, which are stated to be useful in the treatment of degenerative diseases.

Strasser et al., German Patent Application DE 4141218, published Jun. 17, 1993, disclose a series of thiadiazolidin-3-one 1,1-dioxide derivatives as intermediates in the synthesis of various 1,1-dioxo-[1,2,6]thiadiazinecarboxamides which are stated to be potentially useful as analgesics, antipyretics and inflammation inhibitors.

Hlasta et al., European Patent Application No. 547708, published Jun. 23, 1993, disclose various 2-substituted saccharin derivatives which are stated to be useful in the treatment of degenerative diseases.

SUMMARY OF THE INVENTION

The invention relates to compounds of the Formula I:

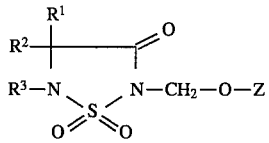

wherein $R^1$ is hydrogen, lower-alkyl, or phenyl-lower-alkyl; $R^2$ is hydrogen, lower-alkyl, or phenyl-lower-alkyl; $R^3$ is hydrogen, or lower-alkyl; and -Z is a group of the formula:

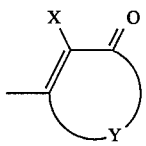

wherein X is hydrogen, halogen, lower-alkoxycarbonyl, lower-alkyl, phenyl, phenyl-lower-alkyl, phenylcarbonyl, lower-alkanoyl, 1-piperidinyl, 4-morpholinyl-lower-alkyl, or phenoxy; and —Y— is the remaining atoms of a monocyclic or bicyclic substituted or unsubstituted heterocyclic ring system; or a pharmaceutically acceptable acid-addition salt thereof; or where applicable, an enantiomer or a racemic mixture thereof.

The compounds of the present invention inhibit the activity of serine proteases, specifically human leukocyte elastase, and are thus useful in the treatment of degenerative disease conditions such as emphysema, rheumatoid arthritis, pancreatitis, cystic fibrosis, chronic bronchitis, adult respiratory distress syndrome, inflammatory bowel disease, psoriasis, bullous pemphigoid, periodontal disease, and alpha-1-antitrypsin deficiency.

Preferred compounds of the Formula I above are those wherein $R^1$, $R^2$, $R^3$ and X are as defined above; and —Y— is —$(CH_2)_m$—O—, —CHR—O—, —$C(R)_2$—O—, —$(CH_2)_m$—N(R')—, —CHR-N(R')—, —$C(R)_2$—N(R')—, —C(R')=C(R')—O—, —C(R')=C(R')—N(R')—, —C(=O)—C(R")=C(R")—, —C(Z')=C(Z')—O—, —C(Z')=C(Z')—N(R')—, —N(Z")—C(Z")=N— or —N=C(Z")—N(Z")— wherein m is 1, 2, 3, or 4, R is the same or different lower-alkyl, phenyl or phenyl-lower-alkyl, R' is H or R, R" is H or R or the R" groups taken together with the carbon atoms to which they are bonded are furano, the Z' groups taken together with the carbon atoms to which they are bonded are benzo, furano, pyrido, pyrimidino or pyridazino, and the Z" groups taken together with the carbon or nitrogen atoms to which they are bonded are pyrido, pyrimidino or pyridazino.

A preferred species of the Formula I above is the compound wherein $R^1$ is hydrogen; $R^2$ is 3-methylbutyl; $R^3$ is methyl; and Z is

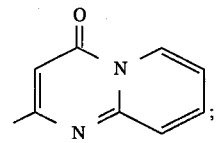

or a pharmaceutically acceptable acid-addition salt thereof; or an enantiomer or a racemic mixture thereof.

The invention further relates to a pharmaceutical composition for the treatment of degenerative diseases which comprises a pharmaceutically acceptable carrier, adjuvant, diluent or vehicle together with an effective proteolytic enzyme inhibiting amount of a compound of the Formula I.

The invention further relates to a method for the treatment of degenerative diseases which comprises administering to a patient in need of such treatment an effective proteolytic enzyme inhibiting amount of a compound of the Formula I.

DETAILED DESCRIPTION INCLUSIVE OF PREFERRED EMBODIMENTS

The term lower-alkyl as used herein means linear or branched hydrocarbon chains having one to about five carbon atoms and thus includes methyl, ethyl, propyl, isopropyl, n-butyl, sec-butyl, 3-methylbutyl; n-pentyl, and the like.

The term halogen or halide as used herein means chlorine, bromine, iodine, and fluorine.

The term lower-alkoxy as used herein means linear or branched alkyloxy substituents having from one to about four carbon atoms and thus includes methoxy, ethoxy, propoxy, isopropoxy, butoxy, sec-butoxy, and the like.

The term lower-alkanoyl as used herein means linear or branched hydrocarbon chains having two to about four carbon atoms and thus includes acetyl, propionyl, isobutyryl, and the like.

The numbering system used throughout this specification is shown in the ring system which is illustrated below. This ring

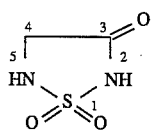

system is named in the chemical literature as a 1,2,5-thiadiazolidin-3-one 1,1-dioxide.

The synthesis of the compounds of the invention may be outlined as shown in Scheme A:

SCHEME A

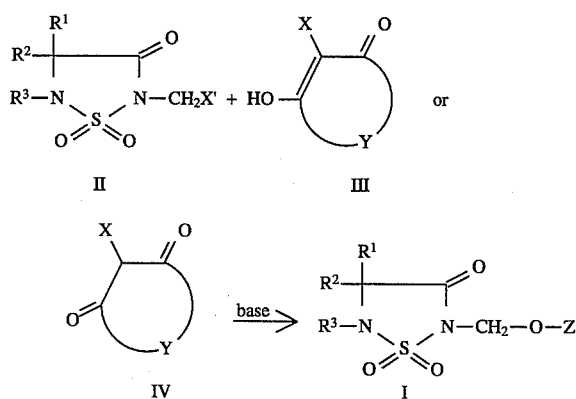

A suitably substituted 2-halomethyl-1,2,5-thiadiazolidin-3-one 1,1-dioxide derivative of the formula II, wherein X is a halogen, preferably chlorine, in a suitable organic solvent, such as dimethylformamide, is treated with an excess of an alcohol of the formula III or a dione of the formula IV, in the presence of an excess of a base, such as potassium carbonate, at a temperature in the range of about room temperature up to the boiling point of the solvent used, preferably at a temperature of about room temperature, to afford the compounds of the formula I,

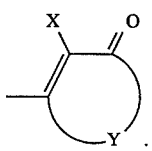

wherein Z is

It will be appreciated that the compounds of the formula I possess an asymmetric carbon at position C-4 of the 1,2,5-thiadiazolidin-3-one 1,1-dioxide ring and are thus capable of existing as enantiomers. Unless otherwise specified herein, the invention is intended to extend to each of the enantiomeric forms including the racemates. In some cases there may be advantages, i.e. greater potency, to using a particular enantiomer when compared to the other enantiomer or the racemate in the treatment of degenerative diseases and such advantages can be readily determined by those skilled in the art. The separate enantiomers may be synthesized from chiral starting materials or the racemates may be resolved by conventional procedures which are well known in the art of chemistry such as chiral chromatography, fractional crystallization of diastereomeric salts and the like.

The compounds of Formula I are useful both in the free base form and in the form of acid-addition salts, and, both forms are within the purview of the invention. The acid-addition salts are often a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not vitiated by side effects ascribable to the anions. In practicing the present invention it is convenient to use the free base form or the hydrochloride, fumarate, toluenesulfonate, methanesulfonate or maleate salts. However, other appropriate pharmaceutically acceptable salts within the scope of the invention are those derived from other mineral acids and organic acids. The acid-addition salts of the basic compounds are prepared by standard procedures well known in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed for purposes of purification or identification, or when it is used as an intermediate in preparing a medicinally acceptable salt by, for example, ion exchange procedures.

The suitably substituted 2-halomethyl-1,2,5-thiadiazolidin-3-one 1,1-dioxides of the formula II, which are required for the synthesis of the compounds of the formula I, can be prepared as shown in scheme B:

SCHEME B

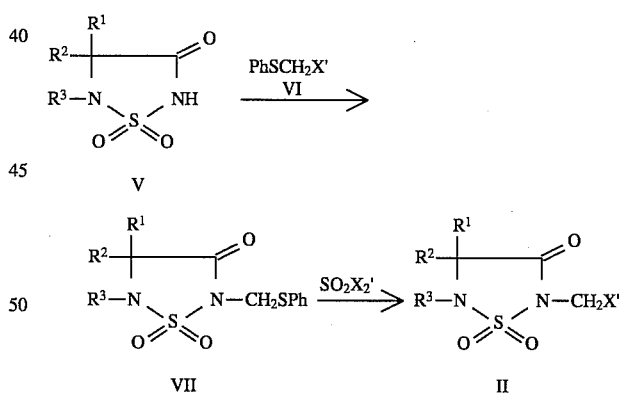

The cesium salt of a suitably substituted 1,2,5-thiadiazolidin-3-one 1,1-dioxide of the formula V, (prepared by the treatment of a compound of the formula V in a lower-alkanol solvent, i.e. methanol, with cesium carbonate at a temperature of about room temperature), in a suitable organic solvent, such as dimethylformamide, is treated with an excess of a halomethyl phenyl sulfide, wherein X' is a halogen, preferably chlorine, at a temperature in the range of about room temperature up to the boiling point of the solvent used, preferably at the boiling point of the solvent used, to afford the compounds of the formula VII. The compound of the formula VII can then be treated with an excess of a sulfuryl halide of the formula $SO_2X_2'$, wherein X' is a halogen, preferably chlorine, in a suitable organic solvent, such as methylene chloride, at a temperature of about room temperature, to afford the compounds of the formula II.

The suitably substituted 1,2,5-thiadiazolidin-3-one 1,1-dioxides of the formula V can be prepared as shown in Scheme C:

SCHEME C

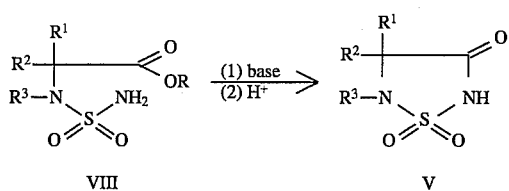

A suitably substituted compound of the formula VIII wherein R is lower-alkyl, in an appropriate lower-alkanol solvent, such as methanol, is treated with an excess of an alkali metal lower-alkoxide; i.e. sodium methoxide, at a temperature in the range of about room temperature up to the boiling point of the solvent used, preferably at a temperature of about room temperature, followed by treatment with a proton source, such as BIO-RAD® 50 W×8 $H^+$ ion exchange resin, to afford the compounds of the formula V.

The compounds of the formula VIII, which are required for the synthesis of the compounds of the formula V, can be prepared as illustrated in Scheme D:

SCHEME D

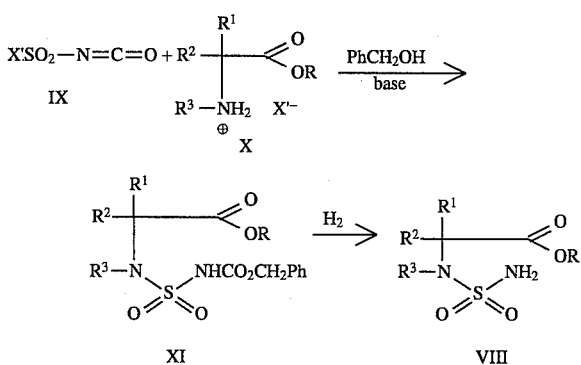

A halosulfonyl isocyanate of the formula IX, wherein X' is a halogen, preferably chlorine, is treated with an excess of an α-amino acid ester of the formula X, wherein R is lower-alkyl and $X'^-$ is a halogen, preferably chlorine, and an excess of benzyl alcohol, in the presence of an excess of a base, such as triethylamine, in an appropriate organic solvent, such as methylene chloride, at a temperature in the range of about −10° C. up to about room temperature, to afford a compound of the formula XI (Note, if desired, the α-amino acid ester can be used as the limiting reagent rather than the halosulfonyl isocyanate). The compound of the formula XI can then be hydrogenated at a hydrogen pressure of about 50 psi, in a lower-alkanol solvent, such as methanol, in the presence of a catalyst, preferably palladium on carbon, to produce the compounds of the formula VIII.

The compounds of the formulas III and IV are either commercially available, or they can be prepared by procedures known in the art (see, for example, allowed U.S. patent application Ser. No. 08/066,805 which is incorporated herein by reference). The halomethyl phenyl sulfides of the formula VI, the halosulfonyl isocyanates of the formula IX, and the α-amino acid esters of the formula X are either commercially available, or they can be prepared by procedures known in the art, or by the procedures described hereinbelow in the examples.

The structures of the compound of the invention were established by the mode of synthesis, and by one or more of elemental analysis, and infrared, nuclear magnetic resonance and mass spectroscopy. The course of the reactions and the identity and homogeneity of the products were assessed by one or more of thin layer chromatography (TLC), high pressure liquid chromatography (HPLC), or gas-liquid chromatography (GLC).

The following examples will further illustrate the invention without, however, limiting it thereto. All melting points (m.p.) are given in degrees centigrade (°C.) and are uncorrected.

EXAMPLE 1

(a)

To a solution of N-t-butoxycarbonyl-sarcosine (50 g; 0.264 mol) in 700 ml of benzene was added 1,8-diazabicyclo [5.4.0]-undec-7-ene (DBU; 40.19 g, 0.264 mol) in one portion. To the above clear solution added 74.94 g (0.528 mol) of methyl iodide in one portion and the resulting clear solution was allowed to reflux for 7 hours. After adding additional methyl iodide (16 ml), the reaction mixture was refluxed with stirring and then cooled to room temperature, and stirred overnight. The reaction mixture was filtered, the residue washed with ether, and the combined filtrate was washed with water, a saturated sodium bicarbonate solution, and then brine. The resulting organic layer was dried over sodium sulfate, filtered, and concentrated in vacuo to afford 46.38 g (86.4%) of N-t-butoxycarbonyl-sarcosine methyl ester as a yellow oil.

(b)

A 2M solution of LDA (70.32 ml, 0.14 mol) was added (via syringe) to a solution of N-t-butoxycarbonyl-sarcosine methyl ester (26 g, 0.1279 mol) in 40 ml of dry THF at −78° C. under nitrogen and the mixture was stirred at this temperature for 30 minutes. To the above mixture was added 4-bromo-2-methyl-2-butene (20 g, 0.134 mol) with stirring continuing at −78° C., and the resulting mixture was allowed to warm to room temperature. The reaction mixture was quenched with 6 ml of saturated ammonium chloride solution at −78° C., 20 ml of water was added, and the resulting reaction mixture was extracted with ethyl acetate. The organic layer was washed with water and brine, dried over sodium sulfate, and concentrated in vacuo to yield a yellow oil, which was purified by silica gel column chromatography (20% ethyl acetate in hexane) to afford 22.1 g (63.7%) of N-t-butoxycarbonyl-2-(3-methyl-2-butenyl)-sarcosine methyl ester as an oil.

(c)

A solution of N-t-butoxycarbonyl-2-(3-methyl-2-butenyl)-sarcosine methyl ester (22.1 g, 81.44 mmol) in 400 ml of methanol under nitrogen was cooled to 0° C. and 1.5 g of 10% Pd/C was added. The mixture was placed into a Parr Apparatus and hydrogenated at 50 psi for 6 hours. The catalyst was removed on a pad of CELITE® and the filtrate was concentrated in vacuo to afford 22.04 g (99%) of N-t-butoxycarbonyl-2-(3-methylbutyl)-sarcosine methyl ester as an oil.

(d)

A mixture of N-t-butoxycarbonyl-2-(3-methylbutyl)-sarcosine methyl ester (22.04 g, 80.62 mmol) in 360 ml of ethereal HCl was stirred at room temperature for 3 days. The resulting mixture was cooled in an ice/bath and the solvent was concentrated in vacuo to afford, after drying, 13.17 g (78%) of 2-(3-methylbutyl)-sarcosine methyl ester hydrochloride (Formula X: R=CH$_3$; R$^2$=(CH$_2$)$_2$CH(CH$_3$)$_2$; R$^3$=CH$_3$; X$^-$=Cl$^-$) which was recrystallized from methanol/ether, m.p. 110°–111° C.

(e)

To a stirred solution of 5.77 ml (66.78 mmol) of chlorosulfonyl isocyanate in methylene chloride was added, under nitrogen, benzyl alcohol (6.89 ml, 66.57 mmol) at 0°–5° C. After stirring the above solution for 1 hour, a solution of 13.166 g (62.78 mmol) of 2-(3-methylbutyl)-sarcosine methyl ester hydrochloride in methylene chloride containing triethylamine (27.33 ml, 194.62 mmol) was added at 0°–5° C. and the resulting mixture was stirred overnight allowing the mixture to warm to room temperature. The reaction mixture was poured into 600 ml of a 10% aq. HCl solution, saturated with sodium chloride, and the organic layer was separated. The aqueous layer was extracted with methylene chloride and the combined organic layer was washed with brine, dried over magnesium sulfate and concentrated in vacuo to yield 21.22 g (87.2%) of N-(carbobenzyloxyaminosulfonyl)-2-(3-methylbutyl)-sarcosine methyl ester (Formula XI: R=CH$_3$; R$^1$=H; R$^2$=(CH$_2$)$_2$CH(CH$_3$)$_2$; R$^3$=CH$_3$) which was purified by silica column chromatography (20% ethyl acetate in hexane) to afford an oil.

(f)

A solution of N-(carbobenylzoxyaminosulfonyl)-2-(3-methylbutyl)-sarcosine methyl ester (20.6 g, 53.17 mmol) in 200 ml of methanol under nitrogen was cooled to 0° C. and 1.5 g of 10% Pd/C was added. The mixture was placed into a Parr Apparatus and hydrogenated for 3.5 hours at 50 psi. The catalyst was removed on a pad of CELITE® and the filtrate was concentrated in vacuo to afford 13.24 g (98.6%) of N-(aminosulfonyl)-2-(3-methylbutyl)-sarcosine methyl ester (Formula VIII: R=CH$_3$; R$^1$=H; R$^2$=(CH$_2$)$_2$CH(CH$_3$)$_2$; R$^3$=CH$_3$) as an oil.

(g)

A solution of N-(aminosulfonyl)-2-(3-methylbutyl)-sarcosine methyl ester (12.28 g, 48.67 mmol) in methanol (150 ml) was added under nitrogen to a solution of sodium methoxide (Na=2.1 g, 95.71 mmol) in 150 ml of ice-cold methanol. The resulting reaction mixture was stirred at room temperature under nitrogen for 1.5 hours, and the mixture was treated with 25 g of ion-exchange resin (BIO RAD® 50W×8H$^+$; 200–400 mesh) for 40 minutes and filtered. The filtrate was concentrated in vacuo to afford 10.7 g (99.8%) of 4-(3-methylbutyl)-5-methyl-1,2,5-thiadiazolidin3-one 1,1-dioxide (Formula V: R$^1$=H; R$^2$=(CH$_2$)$_2$CH(CH$_3$)$_2$; R$^3$=CH$_3$) as a solid, m.p. 212°–214° C.

(h)

A mixture of 4-(3-methylbutyl)-5-methyl-1,2,5-thiadiazolidin-3-one 1,1-dioxide cesium salt (prepared by reacting 7.7 g (34.95 mmol) of 4-(3-methylbutyl)-5-methyl-1,2,5-thiadiazolidin-3-one 1,1-dioxide in methanol with 5.13 g of CS$_2$CO$_3$ followed by removal of the solvent and drying under high vacuum) and phenylthiomethyl chloride (6.65 g, 41.94 mmol) suspended in DMF was heated at 85° C. for 17 hours. The mixture was cooled, and poured into 300 ml of ice/water. The reaction mixture was extracted with ethyl acetate (3×) and the organic layer was washed with water and brine, and dried over sodium sulfate. The organic layer was concentrated in vacuo and the residue was purified by silica column chromatography (10% ethyl acetate in hexane) to afford 8.15 g (70.6%) of 2-phenylthiomethyl-4-(3-methylbutyl)-5-methyl-1,2,5-thiadiazolidin-3-one 1,1-dioxide (Formula VII: R$^1$=H; R$^2$=(CH$_2$)2CH(CH$_3$)$_2$; R$^3$=CH$_3$) as an oil.

(i)

To a solution of 2-phenylthiomethyl-4-(3-methylbutyl)-5-methyl-1,2,5-thiadiazolidin-3-one 1,1-dioxide (8.15 g, 24.66 mmol) in 200 ml of methylene chloride was added in one portion under nitrogen sulfuryl chloride (2.36 ml, 29.6 mmol) and the mixture was stirred for 3.5 hours at room temperature. The mixture was concentrated in vacuo and the residue was triturated in hexane to afford 4.64 g (70%) of 2-chloromethyl-4-(3-methylbutyl)-5-methyl-1,2,5-thiadiazolidin-3-one 1,1-dioxide (Formula II: R$^1$=H; R$^2$=(CH$_2$)$_2$CH(CH$_3$)$_2$; R$^3$=CH$_3$; X'=Cl) as a solid, m.p. 59°–60° C.

(j)

A mixture of 2-chloromethyl-4-(3-methylbutyl)-5-methyl-1,2,5-thiadiazolidin-3-one 1,1-dioxide (1 g; 3.72 mmol), 2,4-dioxo-4-H-pyrido[1,2-a]pyrimidine (Formula IV: X=H; Y=

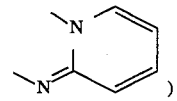

)

(0.72 g; 4.44 mmol), and potassium carbonate (0.67 g; 4.84 mmol) in 35 ml of DMF was stirred at room temperature for 24 hours. The mixture was poured into ice/water, extracted with ethyl acetate, and the organic layer was washed with water, brine, and dried. The solvent was concentrated in vacuo and the residue purified by silica gel flash chromatography (70% hexane/ethyl acetate, 5% methanol/ethyl acetate) to afford 0.29 g of 2-(4-oxo-4-H-pyrido[1,2-a]pyrimidin-2-yl-oxymethyl)-4-(3-methylbutyl)-5-methyl-1,2,5-thiadiazolidin-3-one 1,1-dioxide (Formula I: R$^1$=H; R$^2$=(CH$_2$)$_2$CH(CH$_3$); R$^3$=CH$_3$;

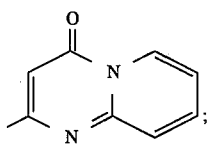

Example 1J) as a solid, m.p. 106.5°–107.5° C., and 0.34 g of 2-(4-oxo-4-H-2-hydroxypyrido[1,2-a]pyrimidin-3-yl-methyl)-4-(3-methylbutyl)-5-methyl-1,2,5-thiadiazolidin-3-one 1,1-dioxide as a solid, m.p. 165°–170° C.

EXAMPLE 2

(a)

Following a procedure similar to that described in example 1(b), but substituting 2.1 equivalents of methyl iodide for 4-bromo-2-methyl-2-butene and utilizing 2.2 equivalents of lithium diisopropyl amide (LDA) it is contemplated that there can be prepared a compound of the formula: $(CH_3)_2C(CO_2CH_3)N(CH_3)(CO_2tBu)$.

(b)

Following a procedure similar to that described in example 1(d), but substituting the compound example 2(a) for the compound of example 1(c), it is contemplated that there can be prepared a compound of the formula $(CH_3)_2C(CO_2CH_3)NH(CH_3) \cdot HCl$.

Following procedures similar to those described in Examples 1(e)–(g), but substituting an appropriate α-amino acid ester of the formula X for the compound of example 1(d), it is contemplated that there can be prepared the following compounds of the formula V illustrated in Table I.

TABLE I

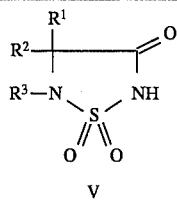

V

| Example No. | $R^1$ | $R^2$ | $R^3$ | Ester Used |
|---|---|---|---|---|
| 3 | $CH_3$ | $CH_3$ | $CH_3$ | $(CH_3)_2C(NHCH_3)CO_2CH_3 \cdot HCl$ |
| 4 | $CH_2Ph$ | H | H | $C_6H_5CH_2CH(NH_2)CO_2CH_3 \cdot HCl$ |

Following a procedure similar to that described in example 1(h) but substituting an appropriate compound of the Formula V for 4-(3-methylbutyl)-5-methyl-1,2,5-thiadiazolidin-3-one 1,1-dioxide it is contemplated that there can be prepared the following compounds of the formula VII illustrated in Table II:

TABLE II

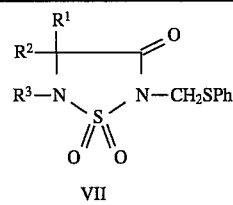

VII

| Example No. | $R^1$ | $R^2$ | $R^3$ |
|---|---|---|---|
| 5 | $CH_3$ | $CH_3$ | $CH_3$ |
| 6 | $CH_2Ph$ | H | H |

Following a procedure similar to that described in example 1(i), but substituting an appropriate compound of the formula VII for 2-phenylthiomethyl-4-(3-methylbutyl)-5-methyl-1,2,5-thiadiazolidin-3-one 1,1-dioxide it is contemplated that there can be prepared the following compounds of the formula II illustrated in Table III:

TABLE III

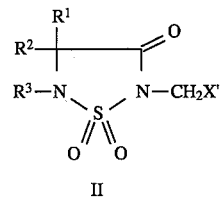

II

| Example No. | $R^1$ | $R^2$ | $R^3$ | X' |
|---|---|---|---|---|
| 7 | $CH_3$ | $CH_3$ | $CH_3$ | Cl |
| 8 | $CH_2Ph$ | H | H | Cl |

Following a procedure similar to that described in example 1(j), but utilizing an appropriate compound of the formula III or IV and, if applicable, substituting an appropriate compound of the formula II for 2-chloromethyl-4-(3-methylbutyl)-5-methyl-1,2,5-thiadiazolidin-3-one 1,1-dioxide, it is contemplated that there can be prepared the following compounds of the formula I illustrated in table IV.

TABLE IV
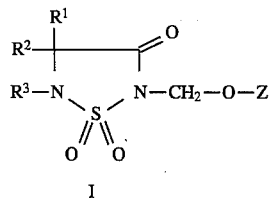
I
| Example No. | R¹ | R² | R³ | z |
|---|---|---|---|---|
| 9 | $CH_3$ | $CH_3$ | $CH_3$ | 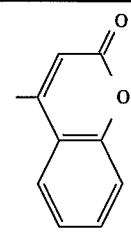 |
| 10 | $CH_2Ph$ | H | H | 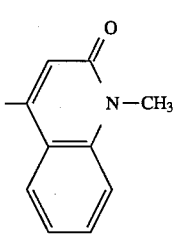 |
| 11 | H | $(CH_2)_2CH(CH_3)_2$ | $CH_3$ | 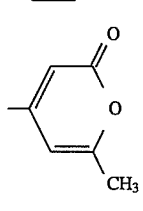 |
| 12 | $CH_3$ | $CH_3$ | $CH_3$ | $C_6H_5C(O)$ 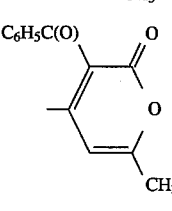 |
| 13 | $CH_2Ph$ | H | H | 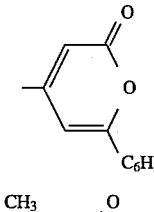 |
| 14 | H | $(CH_2)_2CH(CH_3)_2$ | $CH_3$ | 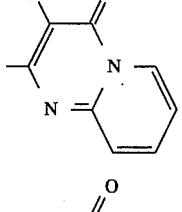 |
| 15 | $CH_3$ | $CH_3$ | $CH_3$ | 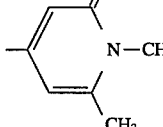 |

TABLE IV-continued
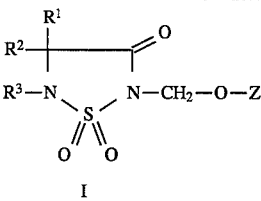
I
| Example No. | R¹ | R² | R³ | z |
|---|---|---|---|---|
| 16 | CH₂Ph | H | H | 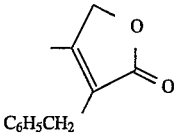 |
| 17 | H | (CH₂)₂CH(CH₃)₂ | CH₃ | 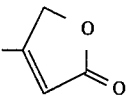 |
| 18 | CH₃ | CH₃ | CH₃ | 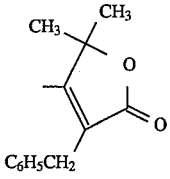 |
| 19 | CH₂Ph | H | H | 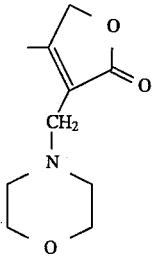 |
| 20 | H | (CH₂)CH(CH₃)₂ | CH₃ | 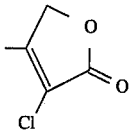 |
| 21 | CH₃ | CH₃ | CH₃ | 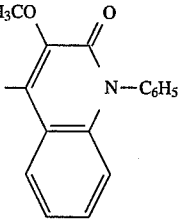 |
| 22 | CH₂Ph | H | H | 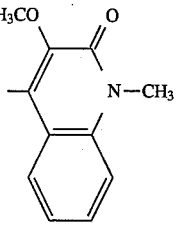 |

TABLE IV-continued

Structure I:
R²-C(R¹)(-NR³-SO₂-N(-CH₂-O-Z)-C(=O)-) (cyclic sulfamide)

| Example No. | R¹ | R² | R³ | Z |
|---|---|---|---|---|
| 23 | H | (CH₂)₂CH(CH₃)₂ | CH₃ | 3-methyl-2-phenyl-furan-2(5H)-one-yl (enol lactone with C₆H₅ substituent) |
| 24 | CH₃ | CH₃ | CH₃ | 2-benzyl-3-methyl-4H-pyrido[1,2-a]pyrimidin-4-one-yl (C₆H₅CH₂ substituent) |
| 25 | CH₂Ph | H | H | 3-methyl-4H-pyrido[1,2-a]pyrimidin-4-one-yl |
| 26 | H | (CH₂)₂CH(CH₃)₂ | CH₃ | 2-chloro-3-methyl-4H-pyrido[1,2-a]pyrimidin-4-one-yl |
| 27 | CH₃ | CH₃ | CH₃ | 3-methyl-5,5-dimethyl-furan-2(5H)-one-yl |
| 28 | CH₂Ph | H | H | 1-phenyl-3-phenoxy-4-methyl-3-pyrrolin-2-one-yl (N–C₆H₅; C₆H₅O substituent) |
| 29 | H | (CH₂)₂CH(CH₃)₂ | CH₃ | 1-phenyl-3-piperidinyl-4-methyl-3-pyrrolin-2-one-yl (N–C₆H₅) |

TABLE IV-continued

Structure I:
$$R^2-\underset{R^1}{\underset{|}{C}}(-C(=O)-)-N(-CH_2-O-Z)-S(O_2)-N(R^3)$$

| Example No. | R¹ | R² | R³ | z |
|---|---|---|---|---|
| 30 | CH₃ | CH₃ | CH₃ | (2-methyl-3-(morpholinomethyl-CH₂)-carbonyl)-pyrido[1,2-a]pyrimidine) |
| 31 | CH₂Ph | H | H | (methyl-methoxy-benzoquinonyl-furan) |
| 32 | H | (CH₂)₂CH(CH₃)₂ | CH₃ | (3,4-dimethyl-5,5-dimethyl-2-(morpholinomethyl)furan-2(5H)-one carbonyl) |
| 33 | CH₂ | CH₃ | CH₃ | (2-chloro-4-methyl-6-methyl-pyranone) |
| 34 | CH₂Ph | H | H | (C₂H₅OC(O)-substituted methyl-pyrimidinyl ketone) |
| 35 | H | (CH₂)₂CH(CH₃)₂ | CH₃ | (2-chloro-3-methyl-pyrido[1,2-a] ketone) |

TABLE IV-continued

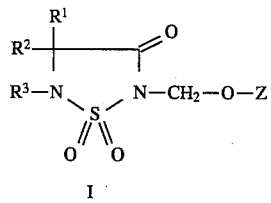

| Example No. | R¹ | R² | R³ | z |
|---|---|---|---|---|
| 36 | CH₃ | CH₃ | CH₃ | 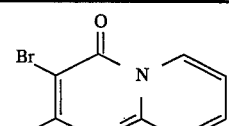 |
| 37 | CH₂Ph | H | H | 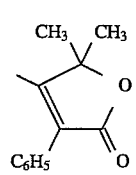 |
| 38 | H | (CH₂)₂CH(CH₃)₂ | CH₃ | 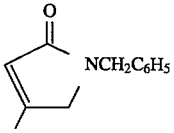 |
| 39 | CH₃ | CH₃ | CH₃ | 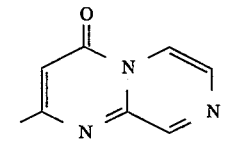 |

Biological Test Results

Representative examples of the compounds of the invention have been found to possess valuable pharmacological properties. In particular, they have been found to inhibit the activity of serine proteases, specifically human leukocyte elastase, and are thus useful in the treatment of degenerative disease conditions such as emphysema, rheumatoid arthritis, pancreatitis, cystic fibrosis, chronic bronchitis, adult respiratory distress syndrome, inflammatory bowel disease, psoriasis, bullous pemphigoid, periodontal disease, and alpha-1-antitrypsin deficiency.

The pharmacological properties of representative examples of the compounds of the invention were demonstrated by the following conventional in vitro biological test procedure.

The test compound (inhibitor) is dissolved in DMSO in a vial to produce an inhibitor stock solution which has a concentration in the range of 200–1000 μM. The inhibitor stock solution is diluted (1:4, 1:16 and 1:64) into assay vials (vials 1, 2 and 3 respectively) containing 2.4 mL of buffer solution (50 mM N-[2-hydroxyethyl]piperazine-N'-[2-ethanesulfonic acid]/NaOH, 500 mM NaCl, pH 7.8 at 25° C.) and DMSO is added so that the total volume in each vial is 3.2 mL. 70 μL, 50 μL, 35 μL and 25 μL of inhibitor from assay vial 1 is placed into the first four wells of a 96-well microtiter plate and each well is made up to 90 μL total volume with the addition of a 25% DMSO/buffer solution. The inhibitor from assay vials 2 and 3 is processed in a similar manner and placed in wells 5–12 respectively to afford a total of 12 different inhibitor concentrations. Four wells (wells 13–16) containing 90 μL of the 25% DMSO/buffer solution but no inhibitor are also run simultaneously with the inhibited wells as a control. 150 μL of substrate solution (prepared by the addition of 500 μL of the human leukocyte elastase (HLE) substrate MeOSuc-Ala-Ala-Pro-Val-pNA (18.7 mM in DMSO) to 19.5 mL of buffer solution) is then added simultaneously into each of the 16 wells and the solution in each well was thoroughly mixed.

The 96-well microtiter plate is placed into a Microplate Reader #89815A spectrophotometer and 110 BL of the enzyme solution (prepared as follows: a mixture of 20 mL of buffer solution and 20 mg of bovine serum albumen is gently vortexed in a scintillation vial and 5 BL HLE stock solution (1 mg/mL dissolved in deionized water) is added) is added simultaneously to each of the 16 wells. Each of the solutions in the wells is throughly mixed and then the time-dependent absorbance data is collected at an absorbance of 410 nM until the assay is complete. It should be noted that although this assay method can be done manually, it is preferred to perform the assay robotically using a Hewlett Packard MicroAssay System Robot.

A plot of the absorbance versus time data thus obtained affords progress curves the final slope of which is equal to the final steady-state velocities (VF). Using the program ENZFITTER (Elsevier software), the progress curves for the four control assays ([I]=0) are fit by linear regression to yield the enzyme reaction velocity values in the absences of inhibit or ($V_o$) which are averaged to produce a single fixed value. The inhibition constant $K_i$(nM) is then obtained from a plot of $$\frac{[I]}{1 - V_F/V_o} \text{ versus } V_o/V_F$$

which affords a linear plot wherein:

$$\text{slope} = K_i \left(1 + \frac{[S]}{K_m}\right)$$

and [S] is the concentration of the substrate and $K_m$ is the Michaelis constant.

A representative compound of the invention, Example 1(j), was tested for human leukocyte elastase inhibitory activity according to the above-described procedure and had a $K_i$ of 0.79 nM.

The compounds of the invention can be prepared for pharmaceutical use by conventional pharmaceutical procedures that are well known in the art; that is, by formulating a pharmaceutical composition which comprises compounds of the invention or their pharmaceutically acceptable salts together with one or more physiologically acceptable carriers, adjuvants, diluents or vehicles, for oral administration in solid or liquid form, parenteral administration, topical administration or aerosol inhalation administration, and the like.

Solid compositions for oral administration include compressed tablets, pills, powders and granules. In such solid compositions, the active compound is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

Preparations according to the invention for topical administration or aerosol inhalation administration include dissolving or suspending a compound of the invention in a pharmaceutically acceptable vehicle such as water, aqueous alcohol, glycol, oil solution or oil-water emulsion, and the like.

If desired, the compounds of the invention can further be incorporated into slow release or targeted delivery systems such as polymer matrices, liposomes, and microspheres.

The percentage of active component in such compositions may be varied so that a suitable dosage is obtained. The dosage administered to a particular patient is variable depending upon the clinician's judgment using as criteria: The route of administration, the duration of treatment, the size and physical condition of the patient, the potency of the active component and the patient's response thereto. An effective dosage amount of the active component can thus readily be determined by the clinician after a consideration of all criteria and using his best judgment on the patient's behalf.

We claim:

1. A compound of the formula:

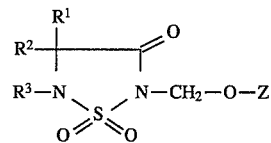

wherein $R^1$ is hydrogen, lower-alkyl, or phenyl-lower-alkyl;

$R^2$ is hydrogen, lower-alkyl, or phenyl-lower-alkyl; $R^3$ is hydrogen, or lower-alkyl; and —Z is a group of the formula:

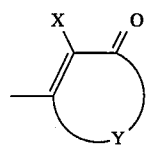

wherein X is hydrogen, halogen, lower-alkoxycarbonyl, lower-alkyl, phenyl, phenyl-lower-alkyl, phenylcarbonyl, lower-alkanoyl, 1-piperidinyl, 4-morpholinyl-lower-alkyl, or phenoxy; and —Y— is —(CH$_2$)$_m$—O—, —CHR—O—, —C(R)$_2$—O—, —(CH$_2$)$_m$—N(R')—, —CHR—N(R')—, —C(R$_2$)—N(R')—, —C(R')=C(R')—O—, —C(R')=C(R')—N(R')—, —C(=O)—C(R")=C(R")—, —C(Z')=C(Z')—O—, —C(Z')=C(Z')—N(R')—, —N(Z")—C(Z")=N— or —N=C(Z")—N(Z")— wherein m is 1, 2, 3, or 4, R is the same or different lower-alkyl, phenyl or phenyl-lower-alkyl, R' is H or R, R" is H or R or the R" groups taken together with the carbon atoms to which they are bonded are furano, the Z' groups taken together with the carbon atoms to which they are bonded are benzo, furano, pyrido, pyrimidino or pyridazino, and the Z" groups taken together with the carbon or nitrogen atoms to which they are bonded are pyrido, pyrimidino or pyridazino.

2. A compound according to claim 1 wherein —Z has one of the following structural formulas:

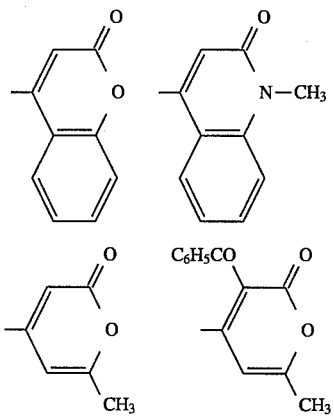

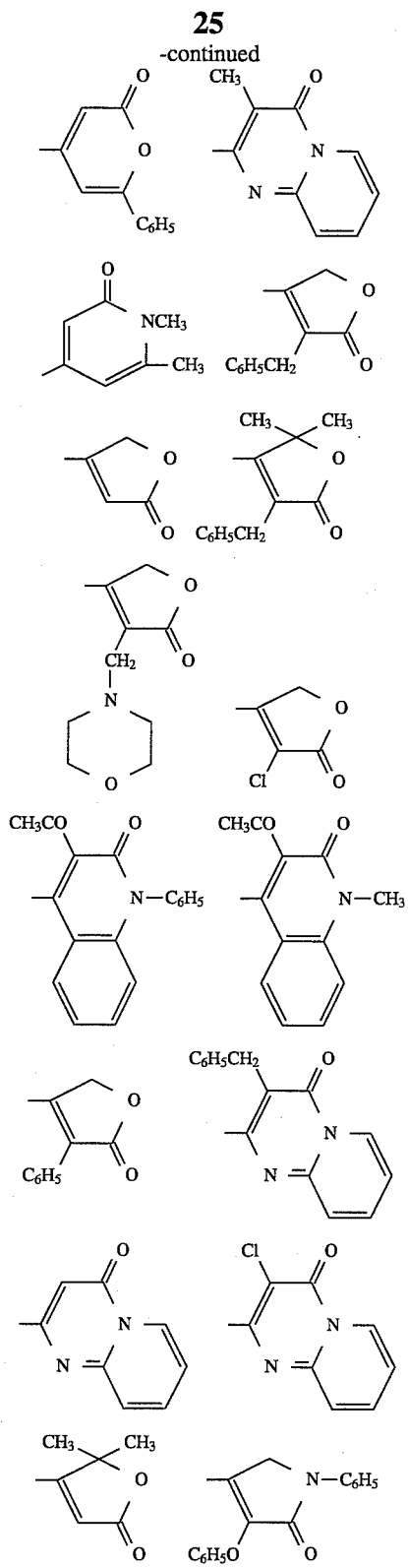
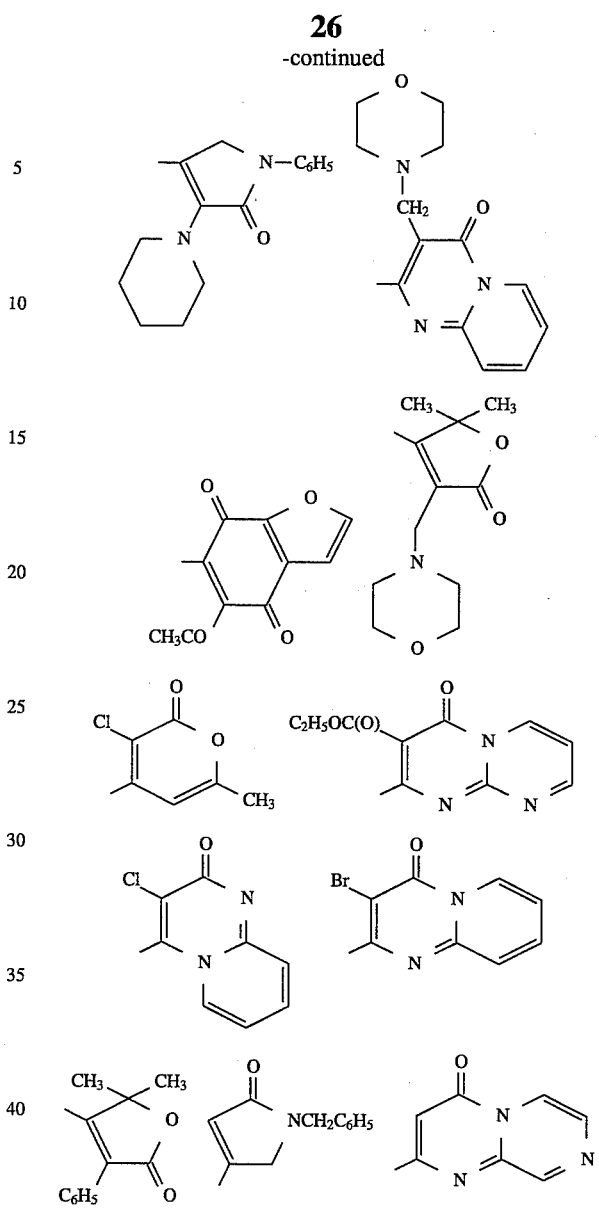
3. A compound according to claim 2 wherein $R^1$ is hydrogen or lower-alkyl; and $R^2$ is hydrogen or lower-alkyl.
4. A compound according to claim 3 wherein $R^1$ is hydrogen or 3-methylbutyl; $R^2$ is hydrogen or 3-methylbutyl; and $R^3$ is methyl.
5. A compound according to claim 4 wherein $R^1$ is hydrogen; $R^2$ is 3-methylbutyl; $R^3$ is methyl; and —Z is
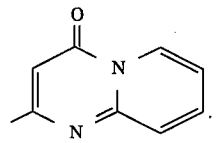

6. A pharmaceutical composition for the inhibition of proteolytic enzymes in a mammal which comprises a pharmaceutically acceptable carrier, adjuvant, diluent or vehicle together with an effective proteolytic enzyme inhibiting amount of a compound according to claim 1.

7. A pharmaceutical composition for the inhibition of proteolytic enzymes in a mammal which comprises a pharmaceutically acceptable carrier, adjuvant, diluent or vehicle together with an effective proteolytic enzyme inhibiting amount of a compound according to claim 2.

8. A pharmaceutical composition for the inhibition of proteolytic enzymes in a mammal which comprises a pharmaceutically acceptable carrier, adjuvant, diluent or vehicle together with an effective proteolytic enzyme inhibiting amount of a compound according to claim 3.

9. A pharmaceutical composition for the inhibition of proteolytic enzymes in a mammal which comprises a pharmaceutically acceptable carrier, adjuvant, diluent or vehicle together with an effective proteolytic enzyme inhibiting amount of a compound according to claim 4.

10. A pharmaceutical composition for the inhibition of proteolytic enzymes in a mammal which comprises a pharmaceutically acceptable carrier, adjuvant, diluent or vehicle together with an effective proteolytic enzyme inhibiting amount of a compound according to claim 5.

11. A method for the inhibition of proteolytic enzymes in a mammal which comprises administering to said mammal in need of such inhibition an effective proteolytic enzyme inhibiting amount of a compound according to claim 1.

12. A method for the inhibition of proteolytic enzymes in a mammal which comprises administering to said mammal in need of such inhibition an effective proteolytic enzyme inhibiting amount of a compound according to claim 2.

13. A method for the inhibition of proteolytic enzymes in a mammal which comprises administering to said mammal in need of such inhibition an effective proteolytic enzyme inhibiting amount of a compound according to claim 3.

14. A method for the inhibition of proteolytic enzymes in a mammal which comprises administering to said mammal in need of such inhibition an effective proteolytic enzyme inhibiting amount of a compound according to claim 4.

15. A method for the inhibition of proteolytic enzymes in a mammal which comprises administering to said mammal in need of such inhibition an effective proteolytic enzyme inhibiting amount of a compound according to claim 5.

16. A method according to claim 1 wherein said inhibition of proteolytic enzymes for the treatment of diseases selected from the group consisting of emphysema, rheumatoid arthritis, pancreatitis, cystic fibrosis, chronic bronchitis, adult respiratory distress syndrome, inflammatory bowel disease, psoriasis, bullous pemphigoid, periodontal disease, and alpha-1-antitrypsin deficiency.

17. A method according to claim 16 wherein said inhibition of proteolytic enzymes for the treatment of diseases selected from the group consisting of emphysema, cystic fibrosis, chronic bronchitis, and adult respiratory distress syndrome.

* * * * *